United States Patent [19]

Di Giovanni

[11] Patent Number: 4,606,344

[45] Date of Patent: Aug. 19, 1986

[54] SURGICAL INSTRUMENT FOR APPLYING FASTENERS HAVING IMPROVED GAP INDICATING MEANS (CASE V)

[75] Inventor: John Di Giovanni, Woodbridge, N.J.

[73] Assignee: Ethicon, Inc., Somerville, N.J.

[21] Appl. No.: 631,117

[22] Filed: Jul. 16, 1984

[51] Int. Cl.⁴ .................. A61B 17/00; A61B 17/12
[52] U.S. Cl. .......................... 128/334 R; 112/169; 128/334 C; 227/DIG. 1
[58] Field of Search .............. 128/334 R, 334 C; 112/169; 227/DIG. 1

[56] References Cited

U.S. PATENT DOCUMENTS

| 4,448,194 | 5/1984 | Di Giovanni | 128/334 R |
| 4,470,532 | 9/1984 | Froehlich | 128/334 R X |
| 4,508,253 | 4/1985 | Green | 227/19 |

Primary Examiner—Lucille M. Phynes
Attorney, Agent, or Firm—Robert L. Minier

[57] ABSTRACT

A surgical instrument for applying tissue fasteners. The instrument includes a stationary jaw and a movable jaw mounted on a support body. The jaws are placed on the opposite sides of the tissue to be joined. The instrument includes an indicator to indicate minute changes in positioning of the jaws.

4 Claims, 8 Drawing Figures

SURGICAL INSTRUMENT FOR APPLYING FASTENERS HAVING IMPROVED GAP INDICATING MEANS (CASE V)

This invention relates to medical instruments and more particularly to instruments for joining tissue organs by using fasteners. Preferably the features are two-piece with one part of the fastener a U-shaped staple and the other part of the fastener a receiver which interlocks with the legs of the staple to form the fastener.

BACKGROUND OF THE INVENTION

Over the years various surgical instruments for joining tissue have been developed. Most instruments have been developed utilizing metal staples for joining the tissue. The metal staples are relatively rigid, have their legs sharpened to readily penetrate the tissue, and once penetrated may then be crimped into a clinched position to hold the tissue together as is well known in the art. Instruments of this type are more fully disclosed and described in U.S. Pat. Nos. 3,080,564, 3,079,606, 2,891,250, 3,589,589, 4,207,898 and 4,351,466.

Generally, the instruments comprise a movable member or jaw and a stationary member or jaw. The movable jaw usually carries the metal staples and the stationary jaw carries an anvil which clinches or bends the legs of the staple that pass through the tissue. In use, the tissue is placed between the jaws, the jaws brought to the appropriate gap and the staples driven through the tissue and clinched to set the staple. A major problem with these instruments is the use of the metal staple. While metal staples provide desired hemostatsis in the joining of the tissue, they remain in the tissue and can disrupt future diagnostic techniques such as x-ray diagnosis, computer axial tomography, nuclear magnetic resonance, and the like. To eliminate this problem, it has been found desirable to develop instruments which can set non-metallic fasteners. These are fasteners made from biologically absorbable or non-absorbable polymeric materials. Examples of such non-absorbable polymeric materials would be the polyolefins, polyesters, and the like. Examples of the absorbable polymeric materials would be the polymers and copolymers of glycolide, lactide, dioxanone, etc. These polymeric materials do not have the dead-bend morphology of a metal and, hence, they cannot be clinched in the same manner as a metal staple. To use these polymers, the fasteners are designed as two-piece fasteners. This means one piece of the fastener is placed on one side of the tissue to be joined and the second piece of the fastener is placed on the other side of the tissue to be joined. One piece of the fastener is a U-shaped staple which has legs which are caused to penetrate the tissue. On the opposite side of the tissue is the second fastener piece or receiver which is a member used to engage the legs to interlock therewith once the legs have penetrated the tissue and, hence, join the tissue together.

As can be appreciated this major change in design and configuration of fasteners causes a number of problems. First, the fasteners must be designed to be sufficiently sharp and strong to penetrate the tissue or in certain instances some aiding means must be used with the fastener to assist in penetrating the tissue. Also, the fasteners must be designed to develop an interlocking between the two pieces.

These differences cause various types of forces to be used when joining the tissue together, and these forces are different from the forces required when joining tissue using metallic fasteners. Also, when utlizing the two-piece fasteners, alignment between the two fasteners is extremely critical. As can be appreciated, when applying these fasteners the instrument must hold the pieces until one piece has penetrated the tissue and the opposite piece is interengaged and locked on to the penetrating portion of the other member. Once this is accomplished the instrument must then release both pieces preferably simultaneously.

A great portion of these operations are carried out deep within the thoracic or abdominal cavities under conditions where visibility is usually poor. An intrical step in the operation of the instrument is to set a correct gap between the jaws of the instrument before the fasteners are placed. This gap is intrical in order to be certain the tissue is joined and hemostasis will occur. If the gap is too large excess bleeding will occur and desired healing of the wound delayed. If the gap is too small necrosis of the tissue may occur.

It is an object of the present invention to provide an instrument that clearly indicates to the user when a desired gap has been obtained. It is a further object of the present invention to provide instruments that are reliable as well as operate and function in identical manners. It is yet another object of the present invention to provide an instrument that is economical to manufacture especially in view of today's concern for reducing medical and surgical costs.

Also the gap measurements are in extremely small units and the difference between a desirable gap and an undesirable gap may be a fraction of a millimeter. It is an object of the present invention to provide an instrument that clearly indicates very small differences in gap settings.

SUMMARY OF THE PRESENT INVENTION

The present invention provides a surgical instrument for joining tissue by means of staples or other fasteners. The fasteners may usually comprise a U-shaped staple member with or without a receiver for engaging with the legs of said staple member. The instrument places the staple member on one side of the tissue to be joined and the receiver, if one is used, on the opposite side of the tissue. The instrument causes the staple legs to penetrate the tissue and engage and interlock with the receiver or it may merely crimp the staple legs when no receiver is used. The instrument comprises a support body. Mounted at one end of the support body is a pair of jaws. A staple housing is mounted in one of the jaws and this jaw is movable with respect to the other of said jaws. Means are mounted in the support body for moving the jaw housing the staples towards the stationary jaw to close the gap between the jaws and clasp the tissue therebetween. Drive means are mounted on the support body for driving the staples from the jaw in which the staple housing is mounted towards the opposite jaw. Actuating means are mounted at the end of the support body opposite the end at which the jaws are mounted for actuating the staple drive means. Preferably cooperating with the open end of the jaws is a means to hold tissue in place between the jaws while the staples are being driven.

The instrument includes means for indicating when a desired gap for joining tissue has been set between the jaws. The indicating means is mounted adjacent to the activating means so that it is readily visible when operating the instrument. The indicating means indicates the gap in multiples of the actual gap being set to allow for accuracy when setting the gap. The indicating means comprises a pivotally mounted pointer. In a preferred embodiment of the present invention the pointer is spring mounted so as to resist movement from its original position. The indicating means includes a member disposed from the means for moving the jaw housing the staples so as to contact the pointer immediately adjacent the pivot point of the pointer whereby slight movement of the means for moving the jaw causes substantially more movement of the free end of the pointer. The indicating means also includes a scale to measure the movement of the pointer and determine when a desired gap between the jaws is set. Other features and details of the present invention will be discussed in the ensuing detailed description and drawings.

DETAILED DESCRIPTION OF THE DRAWINGS

Figure 1:
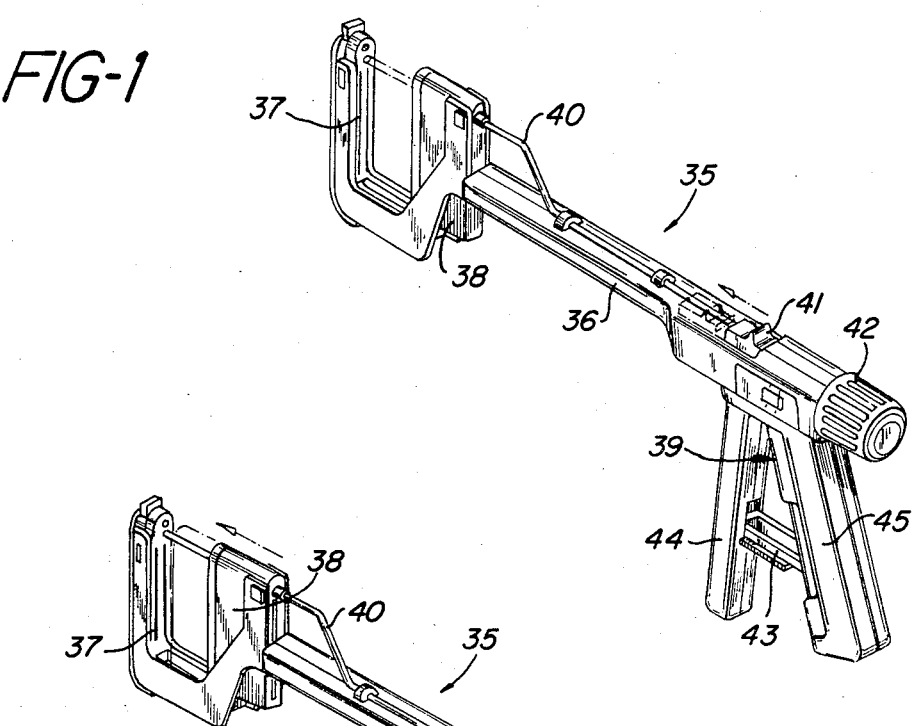
FIG. 1 is a perspective view of an instrument according to the present invention in its fully opened position.
Figure 2:
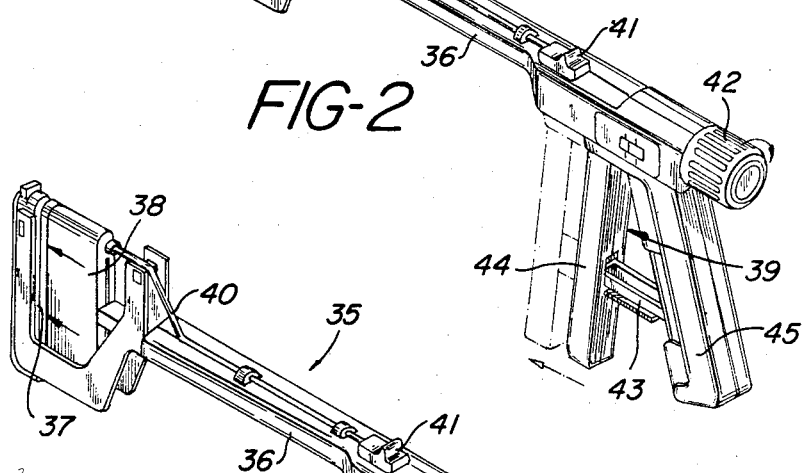
FIG. 2 is a perspective view of the instrument of FIG. 1 in a partially open position
Figure 3:
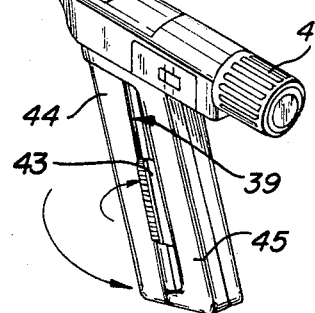
FIG. 3 is a perspective view of the instrument of FIG. 1 in its firing position

Referring to the drawings, in FIGS. 1, 2 and 3 there is depicted a surgical instrument 35 of the present invention useful for joining tissue. The instrument is depicted in three different positions.

In FIG. 1, the instrument is shown in the fully open position. The instrument comprises a support body, 36. A pair of jaws 37 and 38 are positioned at one end of the support body. Mounted the opposite end of the support body is means 39 for actuating the instrument. In FIG. 1, the jaws of the instrument are in the open position ready to be placed about the tissue to be joined.

In FIG. 2, the jaws have been moved closer to one another to produce an appropriate gap to clamp tissue in position between the jaws so that the tissue is ready to be stitched together.

FIG. 3 shows the instrument after it has been actuated and the tissue has been joined by the instrument.

One of the jaws 37 is stationarily mounted at one end of the support body 36. This jaw carries a plurality of receivers of the two-part fastening members used with the instruments of the present invention. The opposite jaw 38, carries the U-shaped fastening members, and is movably mounted on the support body. The tissue to be joined is placed between the two jaws and the movable jaw positioned with respect to the stationary jaw at an appropriate gap. Once the tissue is placed between the jaws, the locking arm 40 is moved forwardly by the pusher 41 to insure that the tissue is held between the jaws. Once the arm is set and engaged by the stationary jaw, the knob 42 at the opposite end of the support body is turned to move the movable jaw towards the stationary jaw and set the appropriate gap between the jaws. Once the gap has been appropriately set, the trigger locking lever 43 may be disengaged and the movable portion 44 of the actuating trigger means moved towards the stationary portion 45 of the trigger means to cause an appropriate pusher to drive the staples forward causing the legs of the staples to penetrate the tissue between the jaws and the legs of the staples to enter the appropriate receivers held in the stationary jaw. Once this is accomplished the knob 42 may be turned in the opposite direction to open the jaws, the locking lever pushed back and the joined tissue separated from the jaws of the instrument.

Figure 4:
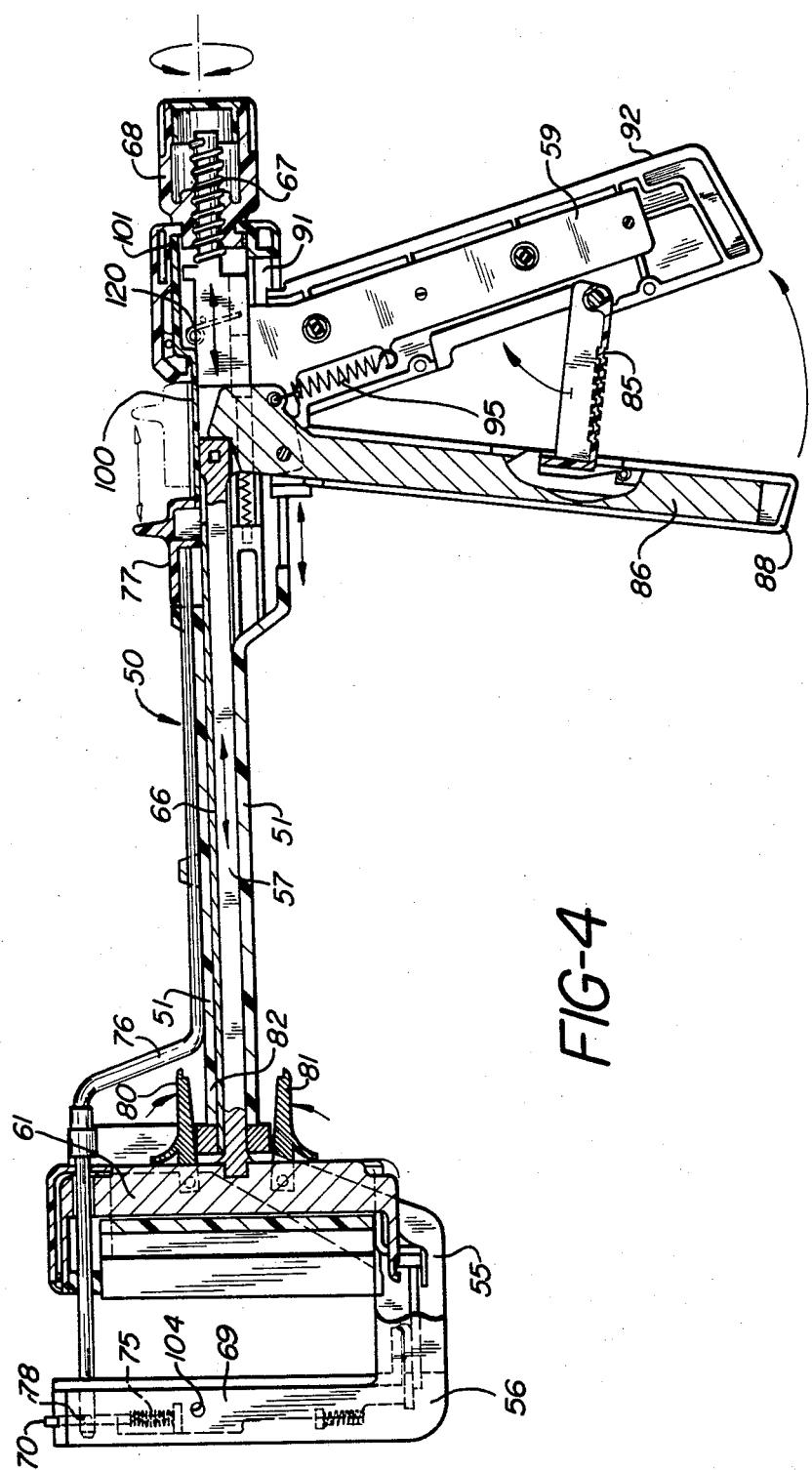
FIG. 4 is a cross-sectional another embodiment of a surgical instrument according to the present invention.
Figure 5:
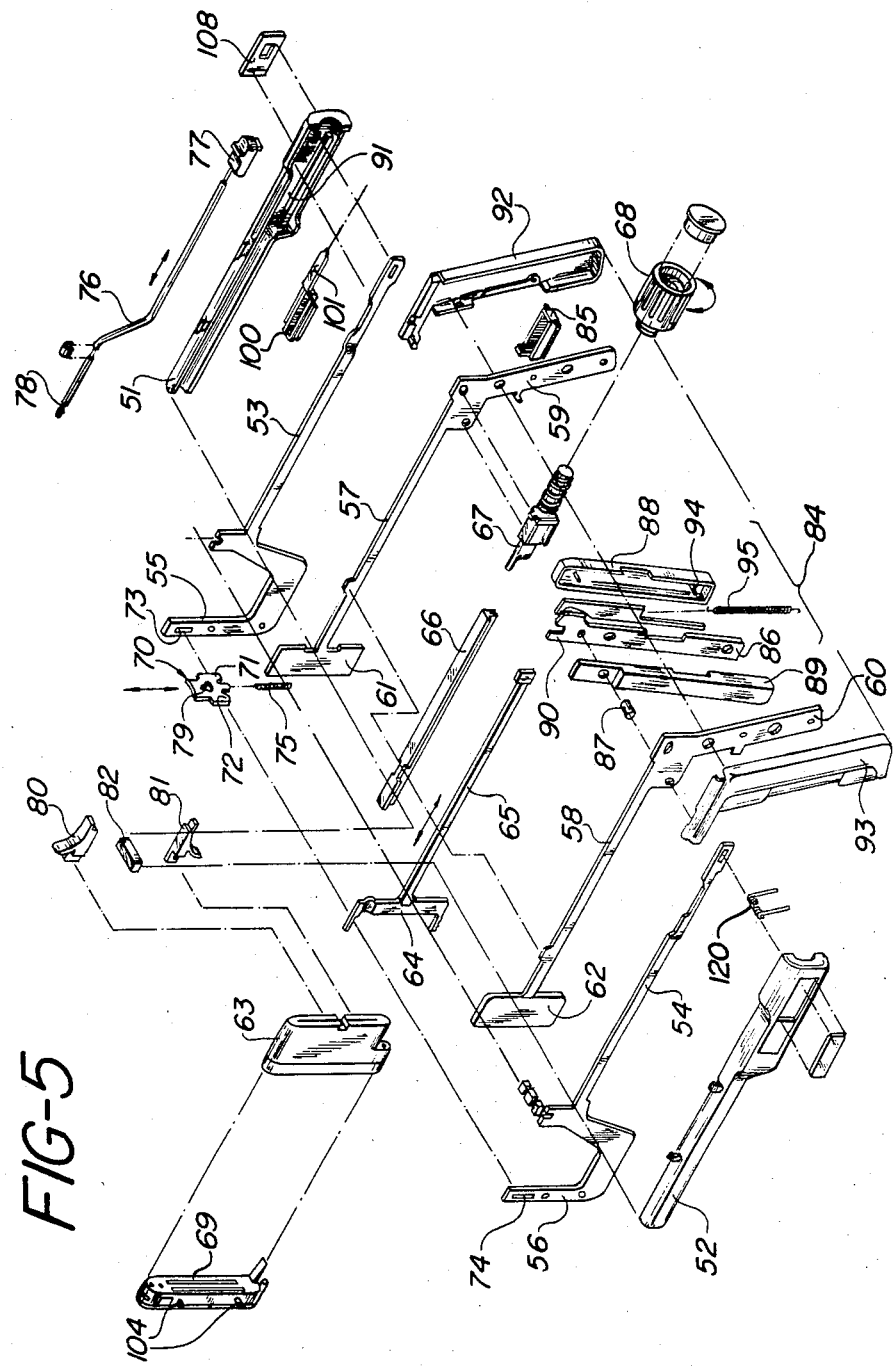
FIG. 5 is an exploded perspective view of the surgical instrument of FIG. 4.

FIG. 4 is a cross-sectional view of one embodiment of a surgical instrument according to the present invention and FIG. 5 is an exploded perspective view showing the different parts of the surgical instrument shown in FIG. 4. The body 50 of the instrument comprises a pair of outer cover members 51 and 52 which when pressed together form a hollow opening longitudinally disposed therebetween. Mounted in this opening are a pair of shafts 53 and 54 which, at one end, carry stationary supports 55 and 56 which together form the stationary jaw. The jaw is held together by riveted pins 104 located in holder 69. Also carried in the opening is a second pair of shafts 57 and 58 which carry at one end the supports 59 and 60 for the stationary portion of the actuating means and at the opposite end carry the supports 61 and 62 for the movable jaw. A holder 69 for the receiver portions of the fasteners is mounted between the stationary jaw supports and the holder 63 for the U-shaped staple portion of the fasteners is mounted between the movable jaw supports 61 and 62. A pusher 64 is mounted on a shaft 65 disposed in the center of the opening formed by the outer cover members. Mounted on top of the center shaft 65 is a movable member 66. The movable member is appropriately mounted through a screw 67 to the knob 68. Turning of the knob in one direction moves the pusher and the staple holder forwardly towards the receiver holder to set an appropriate gap between the staples and the receivers. Turning the knob in the opposite direction moves the pusher and staple holder away from the receiver holder to open the gap and allow tissue to be removed from between the staple holder and receiver holders.

Figure 8:
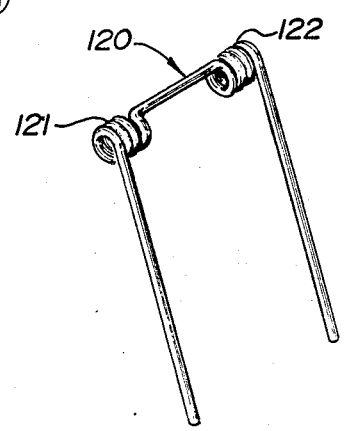
FIG. 8 is an enlarged perspective view of one form of pointer useful with the indicating means of the instrument of the present invention.

Mounted between the supporting jaw members at the top thereof is a portion of means for holding tissue between the jaws and for locking the top of the jaws together to provide rigidity. This portion comprises a movable slotted member 70 having a pair of ears 71 and 72. The ears are disposed in slots 73 and 74 disposed in stationary supports 55 and 56. A compression spring 75 is mounted beneath the slotted member to allow the member to move up and down in the slots disposed in the stationary jaw members. Mounted on top of the outer cover members 51 and 52 and longitudinally thereto is the cooperating portion of the means for holding tissue and locking the jaws together for rigidity. This cooperating portion is a longitudinal movable member 76 that fits through an opening in the upper portion staple holder member 63. The longitudinally movable member is movable forwards and backwards with respect to the outer cover and is moved by the thumbs press 77. The movable member has a slot 78 at its free end and when moved forwardly, interlocks with the opening 58 in the movable slot member 70. A tab depends from the thumb press and fits into grooved member 100 mounted at the back and on top of the cover members. At the opposite end of the groove is a portion 101 that extends inwardly and engages in a slot in the knob 68. The portion 101 is guided in its movement by outer covers 51 and 52. Until the member is pushed as far forwardly as possible to remove the portion 101 from the slot in the knob, the knob cannot be rotated. Mounted from the staple holder are a pair of pawls 80 and 81 and mounted on the rigid shifts 53 and 54 is an anchor 82. The pawls are so disposed as to interlock with the anchor when the appropriate gap is set between the staple holding member 63 and the receiving holding member 69. The interlocking pawls and anchor provide added rigidity to the instrument and allow greater forces to be used when driving the staples through the tissue and into locking relationship with the receivers. At the opposite end of the instrument is mounted the trigger or actuating means 84. The actuating means comprises a movable trigger portion mounted between the supports 57 and 58 by a pin 87. A pivotal member 86 is encased by interlocking plastic handle halves 88 and 89 of the movable trigger portion. The pivotal member 86 includes an ear 90 which engages the shaft 65. The actuating means 84, members 61 and 62 and the shaft 65 are slideably mounted in slot 91 in the outer cover members 51 and 52. The stationary trigger portion comprises a pair of plastic handle halves 92 and 93. Mounted between the pivotal trigger and the stationary trigger is a pivotal interlocking member 85. This member is pivotally mounted between the stationary handles 92 and 93 and interlocks by engaging a pin 94 and spring 95 mounted in the movable portion of the trigger member. Mounted from the cover member 52 is an indicating means to tell when the correct gap is attained between the receiver holder and the staple holder. The indicating means comprises a pivotally mounted pointer 105 that includes a spring resist. An ear on the movable screw portion 67 contacts the pointer. Appropriate cover plate 108 is for identification and to see the movement of the pointer are placed on the outside of the cover members. The indicating means is more fully described in conjunction with FIGS. 6, 7 and 8.

Figure 6:
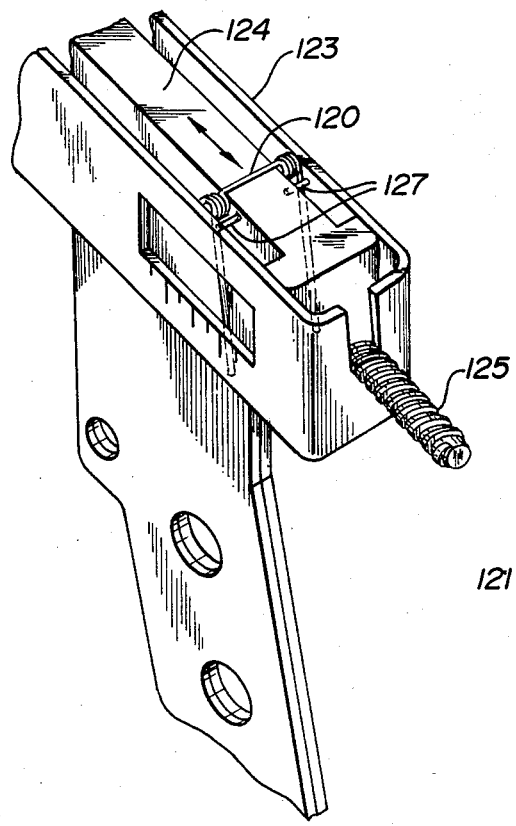
FIG. 6 is an enlarged perspective view of the inside of a portion of an instrument of the present invention depicting the indicating means for identifying the gap setting.
Figure 7:
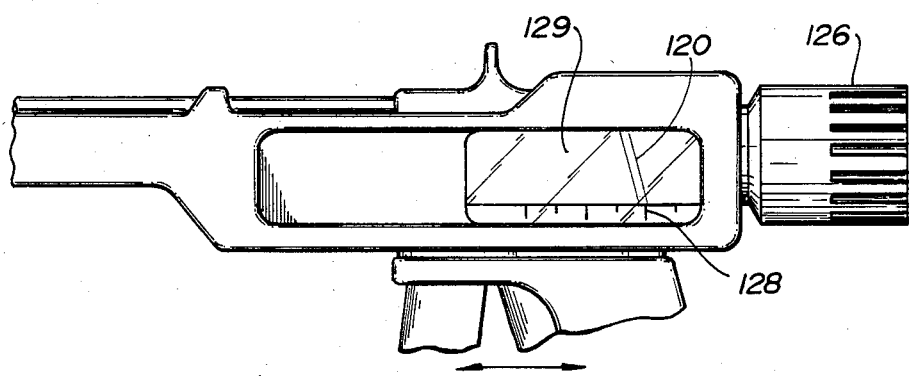
FIG. 7 is a side view of a portion of an instrument of the present invention showing the scale for measuring the gap that has been set.

In FIG. 6 there is shown in perspective a preferred embodiment of the indicating means of the present invention. The indicating means comprises a pointer portion 120. As more clearly shown in FIG. 8, the pointer portion is a U shaped member with a left hand wound spring 121 at one side of one leg and a right hand wound spring 122 at the other site of the other leg. The pointer is mounted in the instrument by attaching the end of the spring 121 and 122 to the stationary portion of the instrument 123. Mounted on the movable shaft 124, which has the movable jaw of the instrument mounted at one end and is connected to the turning screw 125 and knob 126 at the other end, is a pair of ears 127. These ears contact the pointer in the area immediately adjacent to the springs. As more clearly seen in FIG. 7, a suitable scale 128 is mounted on the outside of the instrument adjacent an opening 129 in the instrument. The pointer appears in the opening as the knob is turned and the desired gap is approached. A small movement of the ears 127 causes a relatively large movement of the pointer to allow the gap to be set with excellent accuracy. As may be appreciated the instruments of the present invention may be made from metals, plastics, woods, similar materials or various combinations thereof. If it is desired to make the instruments disposable, then the more inexpensive materials should be used. In most instances, it is desirable to make the instruments disposable because they are relatively complicated intricate mechanisms which are difficult to resterilize.

The general operation of the instruments of the present invention is as follows. The tissues to be joined are placed between the stationary jaw and the movable jaw and are clamped in the space therebetween by moving the tissue locking member in the direction of the stationary jaw to interlock therewith. The tissue locking member aligns the jaws and once engaged allows the gap setting knob to be turned. On turning the gap setting knob the staple housing with the staples and the pusher and drive means is moved towards the stationary jaw. An appropriate gap, generally corresponding to the thickness of the tissues to be joined, is formed between the pair of jaws and is shown on the gauge. Thereafter, the interlock on the trigger mechanism is moved out of the way and the movable handle of the trigger mechanism actuated. This action forces the head of the pusher through the staple housing forcing the staples out of their holder through the tissue so that the legs pierce the tissue and engage the openings of the receivers held by the stationary jaw. Once the staple legs are engaged in the openings of the receivers, the friction holding means of the receivers is disengaged as well as the tissue locking member. After the joining operation has been completed, the gap between the jaws is opened by turning the gap control knob in the opposite direction.

It will be obvious to those skilled in the art that various modifications and changes may be made in the invention without departing from the spirit and scope thereof. The invention is not meant to be limited by that which is shown in the drawings and described in the specification. These changes and modifications are considered to fall within the scope of the present invention as defined by the appended claims.

What is claimed is:

1. Is a surgical instrument for stitching tissue by means of staples said instrument comprising: a support body, a pair of jaws mounted at one end of said support body, a staple housing mounted in one of said jaws, means mounted on said support body for moving said jaw containing said staple housing towards the other jaw to close the gap and clamp tissue placed therebetween, drive means mounted on said support body for driving the staples from the jaw on which the staple housing is mounted towards the opposite jaw, actuating means mounted at the end of said support body opposite said end on which the jaws are mounted for actuating said staple drive means, the improvement comprising indicating means mounted adjacent the actuating means for indicating when an appropriate gap has been set between the jaws, said indicating means comprising a pointer member pivotally mounted at one end thereof to the support body with the other end of said pointer being a free end, a member mounted on the means for moving the jaw containing the staple housing to contact the pointer member adjacent its pivotal mount whereby slight movement of the means for moving the jaw containing the staple housing causes substantial movement of the free end of the pointer member.

2. A surgical instrument according to claim 1 wherein the pointer member is spring mounted to resist movement and cause it to continually return to its originally mounted position.

3. A surgical instrument according to claim 1 or 2 including an opening in the support body through which the pointer may be viewed.

4. A surgical instrument according to claim 3 including side means on the support body adjacent to the opening to indicate the distance of the gap between the jaws of the instrument.

* * * * *